United States Patent
Nomura et al.

(10) Patent No.: US 12,197,015 B2
(45) Date of Patent: Jan. 14, 2025

(54) OPTICAL FIBER CONNECTION STATE DETERMINATION SYSTEM AND OPTICAL FIBER CONNECTION STATE DETERMINATION METHOD

(71) Applicant: FURUKAWA ELECTRIC CO., LTD., Tokyo (JP)

(72) Inventors: Yoshiki Nomura, Tokyo (JP); Ryo Kawahara, Tokyo (JP); Kyosuke Yamauchi, Tokyo (JP); Shunichi Matsushita, Tokyo (JP); Kengo Watanabe, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 223 days.

(21) Appl. No.: 17/819,027

(22) Filed: Aug. 11, 2022

(65) Prior Publication Data
US 2022/0381992 A1   Dec. 1, 2022

Related U.S. Application Data

(63) Continuation of application No. PCT/JP2021/006438, filed on Feb. 19, 2021.

(30) Foreign Application Priority Data

Feb. 20, 2020   (JP) ................. 2020-026825

(51) Int. Cl.
*G02B 6/38*   (2006.01)
*A61B 18/22*   (2006.01)
(Continued)

(52) U.S. Cl.
CPC ............. *G02B 6/385* (2013.01); *G01M 11/31* (2013.01); *G02B 6/3895* (2013.01); *A61B 2018/2247* (2017.05); *A61B 18/24* (2013.01)

(58) Field of Classification Search
CPC ........ G02B 6/385; G01M 11/31; A61B 18/24; A61B 2018/2247; A61B 2018/00595
See application file for complete search history.

(56) References Cited

U.S. PATENT DOCUMENTS

| 11,129,592 B2 | 9/2021 | Horiike et al. |
| 2005/0185957 A1 | 8/2005 | Ohtani et al. |
(Continued)

FOREIGN PATENT DOCUMENTS

| JP | 2002-291764 A | 10/2002 |
| JP | 2004-125711 A | 4/2004 |
(Continued)

OTHER PUBLICATIONS

International Search Report issued May 18, 2021 in PCT/JP2021/006438, filed on Feb. 19, 2021, 2 pages.
(Continued)

*Primary Examiner* — Edmond C Lau
*Assistant Examiner* — Joshua M Carlson
(74) *Attorney, Agent, or Firm* — Oblon, McClelland, Maier & Neustadt, L.L.P.

(57) ABSTRACT

An optical fiber connection state determination system determines a state of connection between a first optical fiber configured to propagate a test light input from a light source and a second optical fiber in a connector configured to detachably connect an output side from which the test light is output in the first optical fiber and an input side of the second optical fiber to which the test light propagated by the first optical fiber and output from the first optical fiber is input, and includes: a measurement unit configured to measure an intensity of a reflected light reflected and propagating thorough the first optical fiber in the test light; and a determination unit configured to determine the state of connection between the first optical fiber and the second
(Continued)

optical fiber in the connector based on the intensity measured by the measurement unit.

13 Claims, 7 Drawing Sheets

(51) Int. Cl.
    *G01M 11/00*     (2006.01)
    *A61B 18/24*     (2006.01)

(56) References Cited

U.S. PATENT DOCUMENTS

| | | | |
|---|---|---|---|
| 2005/0200944 A1* | 9/2005 | Kobayashi | H04B 10/071 |
| | | | 359/333 |
| 2009/0123111 A1 | 5/2009 | Udd | |
| 2009/0137952 A1 | 5/2009 | Ramamurthy et al. | |
| 2013/0090530 A1 | 4/2013 | Ramamurthy et al. | |
| 2014/0226148 A1 | 8/2014 | Lane et al. | |
| 2018/0348443 A1* | 12/2018 | Royer | G02B 6/424 |
| 2019/0373705 A1* | 12/2019 | Hayase | G02B 6/0006 |
| 2020/0249177 A1* | 8/2020 | Tanaka | G01N 21/552 |
| 2021/0068899 A1 | 3/2021 | Nomura et al. | |
| 2023/0084003 A1* | 3/2023 | Taha | G02B 6/4214 |
| | | | 385/31 |

FOREIGN PATENT DOCUMENTS

| | | |
|---|---|---|
| JP | 2014-224898 A | 12/2014 |
| JP | 2015-66056 A | 4/2015 |
| JP | 2016-71040 A | 5/2016 |
| JP | 2018-153564 A | 10/2018 |
| JP | 2019-174256 A | 10/2019 |
| WO | WO 2010/101001 A1 | 9/2010 |
| WO | WO 2019/194188 A1 | 10/2019 |
| WO | WO 2019/230713 A1 | 12/2019 |

OTHER PUBLICATIONS

Extended European Search Report issued Feb. 6, 2024 in European Patent Application No. 21757759.2, 8 pages.

* cited by examiner

OPTICAL FIBER CONNECTION STATE DETERMINATION SYSTEM AND OPTICAL FIBER CONNECTION STATE DETERMINATION METHOD

This application is a continuation of International Application No. PCT/JP2021/006438, filed on Feb. 19, 2021 which claims the benefit of priority of the prior Japanese Patent Application No. 2020-026825, filed on Feb. 20, 2020, the entire contents of which are incorporated herein by reference.

BACKGROUND

The present disclosure relates to an optical fiber connection state determination system and an optical fiber connection state determination method.

There is, as a technique of determining disconnection of an optical fiber, for example, the techniques disclosed in Japanese Laid-open Patent Publication No. 2014-224898, Japanese Laid-open Patent Publication No. 2016-071040 and Japanese Laid-open Patent Publication No. 2002-291764. The technique disclosed in Japanese Laid-open Patent Publication No. 2014-224898 has a configuration for detecting disconnection of an optical fiber by an electronic configuration. The technique disclosed in Japanese Laid-open Patent Publication No. 2016-071040 receives light that is reflected at a distal end of an optical fiber and detects an abnormality in the optical fiber based on a difference from light that is received without disconnection. The technique disclosed in Japanese Laid-open Patent Publication No. 2002-291764 receives light that is reflected on an optical fiber and returns with a light receiving sensor and senses that there is an abnormality in an optical fiber by comparing the result of reception of light to a reference value.

SUMMARY

An apparatus that provides treatment on a patient using laser light connects a laser device that outputs laser light and a catheter that is inserted into a body for each operation and provides treatment by outputting laser light from the catheter. In order to connect the laser device and the catheter for each operation, the laser device and the catheter are configured detachably. If connection of optical fibers between the catheter and the laser device is in an imperfect state when the catheter is connected to the laser device, for example, a situation in which the power of laser light reaching an affected area is insufficient could occur. For this reason, a technique of sensing a state of connection of optical fibers that propagate laser light is desired.

In Japanese Laid-open Patent Publication No. 2014-224898, sensing of disconnection is disclosed but there is no disclosure on sensing a poor connection. In Japanese Laid-open Patent Publication No. 2016-071040, sensing an abnormality in an optical fiber is disclosed but there is no disclosure on determining a poor connection and the technique according to Japanese Laid-open Patent Publication No. 2016-071040 does not make it possible to sense a poor connection. In Japanese Laid-open Patent Publication No. 2002-291764, sensing an abnormality due to a break or a dirt at a facet is disclosed but there is no disclosure on determining a poor connection and the technique according to Japanese Laid-open Patent Publication No. 2002-291764 does not make it possible to sense a poor connection, either.

There is a need for a technique of determining a state of connection of a detachable optical fiber.

According to one aspect of the present disclosure, there is provided an optical fiber connection state determination system for determining a state of connection between a first optical fiber configured to propagate a test light input from a light source and a second optical fiber in a connector configured to detachably connect an output side from which the test light is output in the first optical fiber and an input side of the second optical fiber to which the test light propagated by the first optical fiber and output from the first optical fiber is input, the optical fiber connection state determination system including: a measurement unit configured to measure an intensity of a reflected light reflected and propagating thorough the first optical fiber in the test light; and a determination unit configured to determine the state of connection between the first optical fiber and the second optical fiber in the connector based on the intensity measured by the measurement unit.

According to another aspect of the present disclosure, there is provided an optical fiber connection state determination method for determining a state of connection between a first optical fiber that propagates a test light input from a light source and a second optical fiber in a connector configured to detachably connect an output side from which the test light is output in the first optical fiber and an input side of the second optical fiber to which the test light propagated by the first optical fiber and output from the first optical fiber is input, the method including: a measurement step of measuring an intensity of a reflected light reflected and that propagates thorough the first optical fiber in the test light; and a determination step of determining the state of connection between the first optical fiber and the second optical fiber based on the intensity measured at the measurement step.

DETAILED DESCRIPTION

First Embodiment

Figure 1:
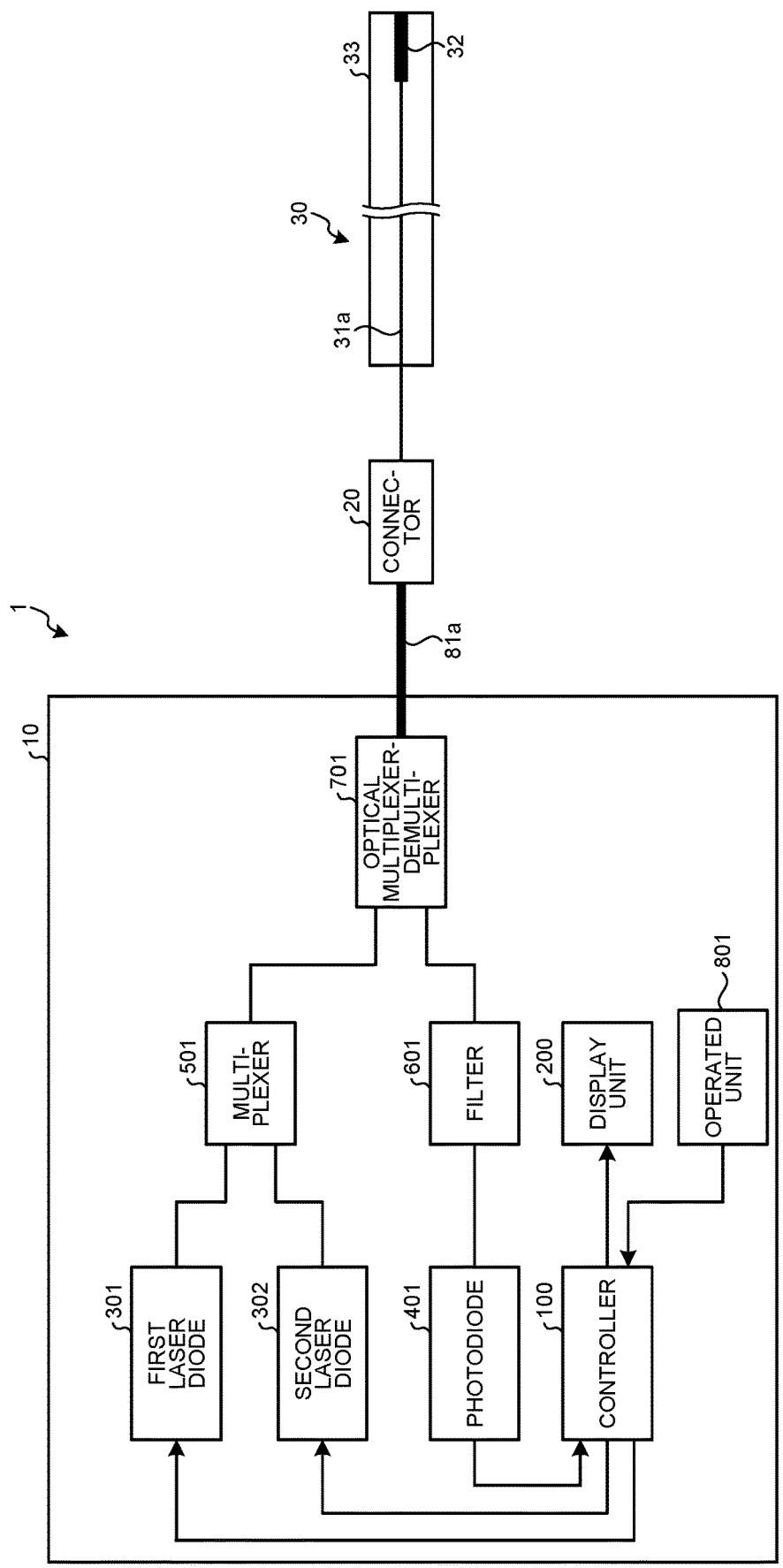
FIG. 1 is a diagram illustrating a schematic configuration of a laser system according to a first embodiment.

Embodiments of the present disclosure will be described in detail below according to the drawings. Note that the embodiments to be described below do not limit the present disclosure. Note that the same or corresponding components are denoted with the same reference numerals as appropriate in the illustration of the drawings.

FIG. 1 is a schematic diagram illustrating a schematic configuration of a laser system 1 according to a first embodiment of the present disclosure. The laser system 1 is a system that provides treatment to a patient by applying laser light to the patient. The laser system 1 includes a laser device 10 that outputs laser light to be applied to the patient, a connector 20 that connects the laser device 10 and a catheter 30, and the catheter 30 that applies the laser light to an affected area of the patient.

In the present embodiment, the laser device 10 includes a first laser diode 301, a second laser diode 302, and a photodiode 401. The laser device 10 includes a multiplexer 501, a filter 601, an optical multiplexer-demultiplexer 701, and a first optical fiber 81a. The laser device 10 further includes a controller 100, a display unit 200, and an operated unit 801. The laser device 10 is an example of a connection state determination system.

The first laser diode 301 is a light source that outputs laser light to be applied to an affected area of the patient. In the following description, the laser light that the first laser diode 301 outputs is referred to as a treatment light. The wavelength of the treatment light in the present embodiment is in a near infrared light band and is, for example, within a range of 600 nm to 1500 nm. The treatment light that is output from the first laser diode 301 is incident on the multiplexer 501 via an optical fiber. The light source that outputs the treatment light is not limited to the laser diode, and the light source may be, for example, a fiber laser.

The second laser diode 302 is a light source that outputs laser light that is used for determining a state of connection of two optical fibers that are connected by the connector 20 and a state of an optical fiber that the catheter 30 includes. In the following description, the laser light that the second laser diode 302 outputs is referred to as test light. The wavelength of the test light in the present embodiment is 635 nm but is not limited to 635 nm, and the wavelength may be another wavelength. The test light that is output from the second laser diode 302 is incident on the multiplexer 501 via an optical fiber. Note that the light source that outputs the test light is not limited to the laser diode.

The multiplexer 501 includes a function of multiplexing a plurality of lights of different wavelengths. The multiplexer 501 multiplexes the treatment light and the test light that are incident via the optical fibers and outputs the treatment light and the test light to the optical multiplexer-demultiplexer 701 via an optical fiber.

The optical multiplexer-demultiplexer 701 outputs, to the first optical fiber 81a via an optical fiber, the treatment light and the test light that are incident from the multiplexer 501 via the optical fiber. The treatment light and the test light that are output from the optical multiplexer-demultiplexer 701 propagate through the first optical fiber 81a. The optical multiplexer-demultiplexer 701 outputs, to the filter 601 via an optical fiber, reflected light that is the laser light having been reflected and having propagated through to the optical multiplexer-demultiplexer 701 in the test light that is output to the first optical fiber 81a. Note that the optical multiplexer-demultiplexer 701 is preferably configured of a 50:50 TAP coupler, an asymmetric TAP coupler or a WDM coupler, or a combination of the couplers.

The first optical fiber 81a is an optical fiber that propagates the treatment light and the test light. The first optical fiber 81a is connected by the connector 20 to a second optical fiber 31a that the catheter 30 to be described below includes. The first optical fiber 81a is, for example, a step-index or grated-index multimode optical fiber but is not particularly limited.

The filter 601 transmits light of a given wavelength in the incident reflected light. Accordingly, the laser light of the wavelength of the treatment light in the reflected light incident on the filter 601 is cut off by the filter 601 and the laser light of the wavelength of the test light passes through the filter 601. The reflected light having passed through the filter 601 is incident on the photodiode 401.

The photodiode 401 is a photodetector and receives the reflected light having passed through the filter 601 and outputs a current signal corresponding to the intensity of the received reflected light. The current signal that is output from the photodiode 401 is input to the controller 100.

The display unit 200 is a liquid crystal display and displays, for example, various types of information on the laser device 10, the state of connection of the optical fibers in the connector 20, and the state of the optical fiber that the catheter 30 includes, using characters, symbols, images, etc. The operated unit 801 includes a button for operating the laser device 10. The operated unit 801 includes a button that switches between outputting the treatment light and stopping outputting the treatment light and a button for starting a process of determining a state of connection of the optical fibers in connection in the connector 20. The operated unit 801 is not limited to the buttons, and the operated unit 801 may be, for example, a touch panel as long as the touch panel receives operations of the operator of the laser device 10.

The controller 100 includes a calculator and a storage unit. The calculator performs control on the first laser diode 301, the second laser diode 302, and the display unit 200 and various types of arithmetic processing for implementing the functions that the laser device 10 includes. The controller 100 consists of a CPU (Central Processing Unit), a FPGA (field-programmable gate array), or both the CPU and the FPGA.

The storage unit includes a part consisting of a ROM (Read Only Memory) and a part consisting of a RAM (Random Access Memory). In the part consisting of the ROM, various programs and data that are used by the calculator to perform arithmetic processing are stored. The RAM is used to store a work space for the calculator to perform arithmetic processing and results of arithmetic processing by the calculator.

Figure 2:
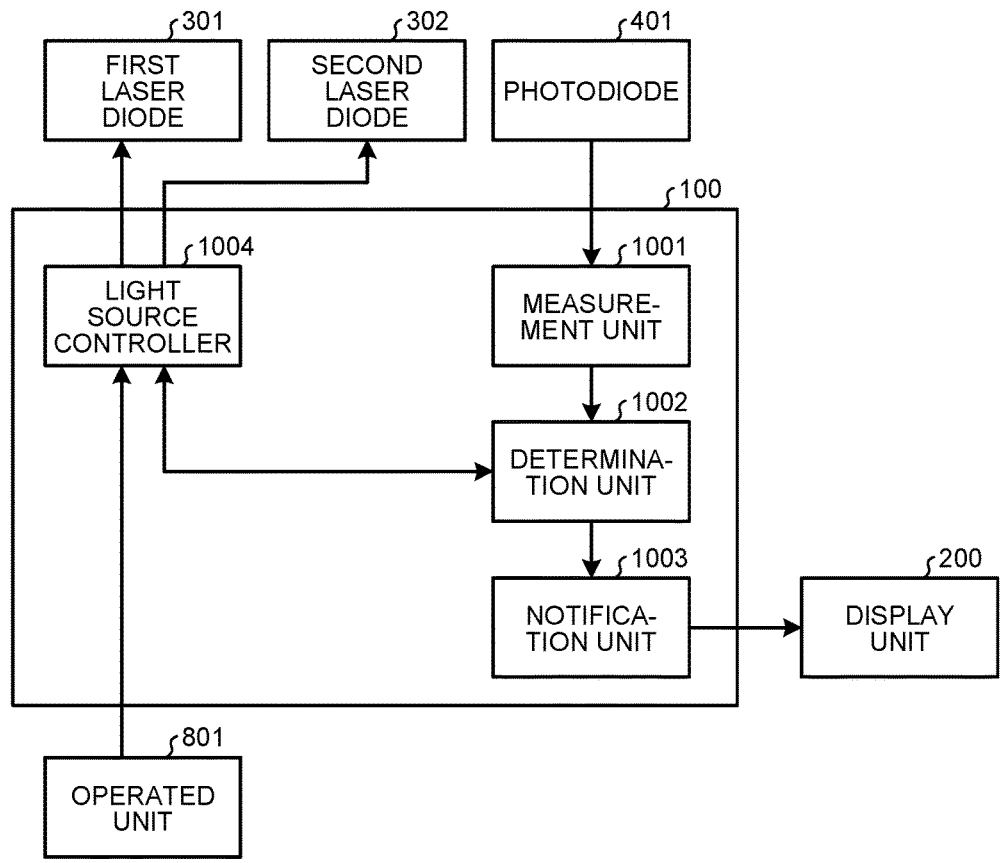
FIG. 2 is a block diagram illustrating a functional configuration according to the first embodiment.

FIG. 2 is a block diagram illustrating a functional configuration according to the present embodiment among functions that are implemented by the calculator by executing the programs that are stored in the storage unit. A measurement unit 1001 acquires the current signal that is output from the photodiode 401. Based on the acquired current signal, the measurement unit 1001 measures an intensity of the reflected light that is incident on the photodiode 401.

Based on the intensity that is measured by the measurement unit 1001, a determination unit 1002 determines a state of connection of the two optical fibers that are connected by the connector 20. Based on the intensity that is measured by the measurement unit 1001, the determination unit 1002 determines whether the optical fiber that the catheter 30 includes is broken.

A notification unit 1003 controls the display unit 200 such that the result of the determination by the determination unit 1002 is displayed on the display unit 200. Accordingly, the user of the laser device 10 is notified of the state of connection of the two optical fibers that are connected by the connector 20 and the state of the optical fiber that the catheter 30 propagating the treatment light includes.

Based on the operation performed on the operated unit 801 and the result of the determination by the determination unit 1002, a light source controller 1004 controls the first laser diode 301 and the second laser diode 302. When the light source controller 1004 outputs a drive signal that drives the first laser diode 301 to the first laser diode 301, a treatment light is output from the first laser diode 301 and, when the light source controller 1004 stops outputting the drive signal to the first laser diode 301, the first laser diode 301 stops outputting the treatment light. When the light source controller 1004 outputs a drive signal that drives the second laser diode 302 to the second laser diode 302, a test light is output from the second laser diode 302 and, when the light source controller 1004 stops outputting the drive signal to the second laser diode 302, the second laser diode 302 stops outputting the test light.

Back to FIG. 1, at least part of the catheter 30 is inserted into the body of the patient to apply the treatment light that is incident from the first optical fiber 81a via the connector 20 to a site to be treated in the patient. The catheter 30 includes a catheter body 33 made of a material that is flexible, such as resin, the second optical fiber 31a that is at least partly inserted into a lumen of the catheter body 33, and a fiber Bragg grating (FBG) 32. The catheter 30 is disposed for each operation and the catheter 30 is connected to the connector 20 before the operation is started and is detached from the connector 20 after the operation.

The second optical fiber 31a is, for example, a step-index or grated-index multimode optical fiber but is not particularly limited. When the catheter 30 is inserted into a blood vessel, the second optical fiber 31a preferably has a small diameter and, for example, the core diameter is 120 µm or smaller and the cladding diameter is 140 µm or smaller. Note that the core diameter and the cladding diameter are an example only and the diameters are not particularly limited to these diameters. As for the second optical fiber 31a, an end of the connector 20 on which the treatment light is incident is referred to as an incidence end and an end that emits the treatment light is referred to as an emission end.

The FBG 32 is provided on the side of an emission end of the second optical fiber 31a and, for example, is connected by fusion to an emission end of the second optical fiber 31a. The FBG 32 transmits the treatment light having been incident from the incidence end of the second optical fiber 31a and having propagated through the second optical fiber 31a. Accordingly, the treatment light exits through the distal end of the second optical fiber 31a (the side of the distal end of the catheter 30). The FBG 32 reflects the test light having been incident from the incidence end of the second optical fiber 31a and having propagated through the second optical fiber 31a. Note that the reflectivity to the test light in the FBG 32 is preferably 90% or more. Setting the reflectivity to the test light in the FBG 32 at 90% or more makes it possible to reflect the test light efficiently.

The connector 20 is a beam magnification connector that detachably connects an output side on which the treatment light and an output light are output in the first optical fiber 81a and an input side on which the treatment light and the output light are input in the second optical fiber 31a. In the connector 20, the first optical fiber 81a and the second optical fiber 31a are connected by, for example, space coupling.

Figure 3:
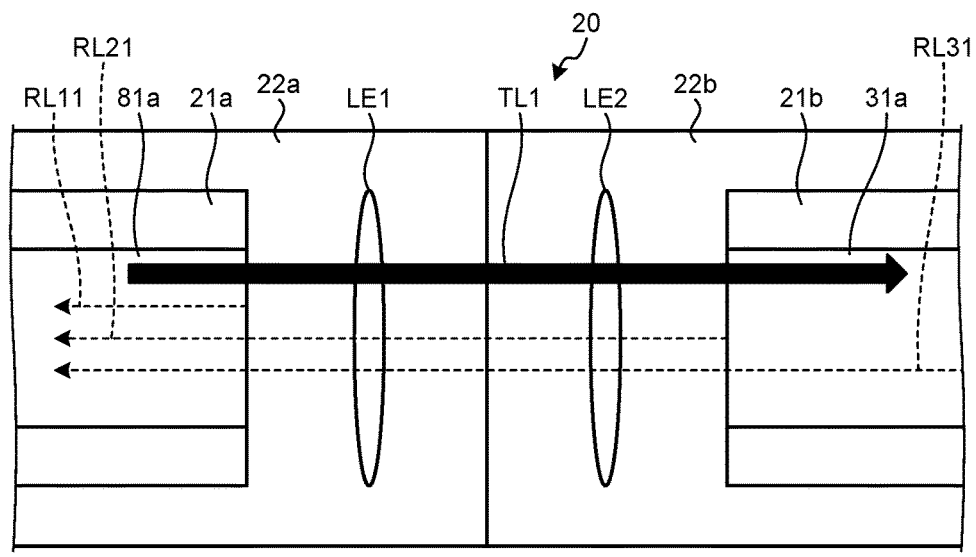
FIG. 3 is a schematic view illustrating an example of a state of connection of optical fibers in a connector.

FIG. 3 is a schematic view illustrating an example of a state of connection of the optical fibers in the connector 20. The connector 20 includes a connector housing 22a and a connector housing 22b. One of the connector housing 22a and the connector housing 22b has a male shape and the other has a female shape and the connector housings are engaged with each other. A ferrule 21a is fixed in the connector housing 22a and fixes an end of the first optical fiber 81a. A first lens LE1 is a convex lens that parallelizes and converges laser light and is fixed in the connector housing 22a. The first lens LE1 turns the laser light that is emitted from the first optical fiber 81a into parallel light. The laser light that is parallelized by the first lens LE1 is incident on a second lens LE2. The first lens LE1 converges the laser light that is incident from the side of the second lens LE2. The laser light that is converged by the first lens LE1 is incident on the first optical fiber 81a.

A ferrule 21b is fixed in the connector housing 22b and fixes an end of the second optical fiber 31a. The second lens LE2 is a convex lens that parallelizes and converges laser light and is fixed in the connector housing 22b. The second lens LE2 converges the laser light that is parallelized by the first lens LE1. The laser light that is parallelized by the second lens LE2 is incident on the first lens LE1. The treatment light is emitted from the distal end of the catheter 30 and therefore the transmittance of the treatment light in the connector 20 is preferably 75% or larger and is more preferably 80% or larger. The transmittance of the test light in the connector 20 is preferably 20% or larger and is more preferably 50% or larger. As long as the transmittance of the test light in the connector 20 is such a transmittance, it is possible to determine a state of connection of the optical fibers in the connector 20.

FIG. 3 schematically illustrates a state in which the first optical fiber 81a and the second optical fiber 31a are connected normally. In FIG. 3, the test light and reflected lights are represented by the arrows and illustration of the treatment light is omitted.

A test light TL1 is the test light that is output from the second laser diode 302. The test light TL1 that is emitted from the first optical fiber 81a is incident on the second optical fiber 31a via the first lens LE1 and the second lens LE2. When the test light TL1 is emitted from the first optical fiber 81a, part of the test light TL1 undergoes Fresnel reflection and serves as a reflected light RL11 and the reflected light RL11 propagates through the first optical fiber 81a. Part of the test light TL1 having reached the second optical fiber 31a undergoes Fresnel reflection at the incidence end of the second optical fiber 31a and serves as a reflected light RL21. A reflected light RL21 reaches the first optical fiber 81a via the second lens LE2 and the first lens LE1 and is incident on the inside of the first optical fiber 81a. When the reflected light RL21 is incident on the first optical fiber 81a, part of the reflected light RL21 undergoes Fresnel reflection.

The test light TL1 having propagated through the second optical fiber 31a is reflected on the FBG 32 and serves as reflected light RL31. The reflected light RL31 propagates in the second optical fiber 31a in a direction opposite to that of the test light TL1. The reflected light RL31 is emitted from the second optical fiber 31a. When the reflected light RL31 is emitted from the second optical fiber 31a, part of the reflected light RL31 undergoes Fresnel reflection. The reflected light RL31 having been emitted from the second optical fiber 31a is incident on the first optical fiber 81a via the second lens LE2 and the first lens LE1. When the reflected light RL31 is incident on the first optical fiber 81a, part of the reflected light RL31 undergoes Fresnel reflection. The reflected light RL11, the reflected light RL21, and the reflected light RL31 are propagated to the photodiode 401 via the first optical fiber 81a, the optical multiplexer-demultiplexer 701, and the filter 601 and the intensity obtained by summing the intensities of the reflected light RL11, the reflected light RL21, and the reflected light RL31 that have been propagated is measured by the measurement unit 1001.

When the intensity of the test light TL1 before being emitted from the first optical fiber 81a is 1 and the transmittance of the pair of the first lens LE1 and the second lens LE2 is β, in the case of the state illustrated in FIG. 3, the intensity obtained by summing the intensities of the reflected light RL11, the reflected light RL21, and the reflected light RL31 is obtained by Expression (1) presented below. Note that the reflectivity of the FBG 32 is set at 100%.

$$0.04+0.96*\beta*(0.04*(*0.96+0.96*0.96*\beta*0.96) \qquad (1)$$

In the present embodiment, the reflectivity of Fresnel reflection at a facet of the optical fiber is set at 4% and 0.04 of the first term of Expression (1) corresponds to the reflected light RL11. Note that "0.96*β" of "0.04+0.96*β* (0.04* . . . " corresponds to the test light that has been emitted from the first optical fiber 81a and that has reached the second optical fiber 31a via the first lens LE1 and the second lens LE2.

"0.04*β*0.96" in the brackets in Equation (1) corresponds to the reflected light RL21 having been incident on the first optical fiber 81a, 0.04 corresponds to the light having reached the second optical fiber 31a and having undergone Fresnel reflection in the test light and, 0.96 corresponds to the light that is incident on the first optical fiber 81a after being reflected on the second optical fiber 31a in the light having passed through the first lens LE1 and the second lend LE2.

"0.96*0.96*β*0.96" in the brackets in Equation (1) corresponds to the reflected light RL31 having been incident on the first optical fiber 81a, the first 0.96 corresponds to the test light incident on the second optical fiber 31a, the following 0.96 corresponds to the light that is emitted from the second optical fiber 31a in the light that is reflected on the FBG 32, and the following 0.96 corresponds to the light incident on the first optical fiber 81a in the light having been emitted from the second optical fiber 31a and having passed through the first lens LE1 and the second lens LE2.

When the transmittance p of the pair of the first lens LE1 and the second lens LE2 is 0.95 in Equation (1), the intensity that is obtained by summing the intensities of the reflected light RL11, the reflected light RL21, and the reflected light RL31 and that is measured by the measurement unit 1001 is an intensity that is 84% of that of the test light TL1. In other words, when the intensity of the reflected light that is measured by the measurement unit 1001 is equal to or larger than the intensity that is 84% of that of the test light TL1, it may be described that the first optical fiber 81a and the second optical fiber 31a are in a state of being connected normally in the connector 20.

Figure 4:
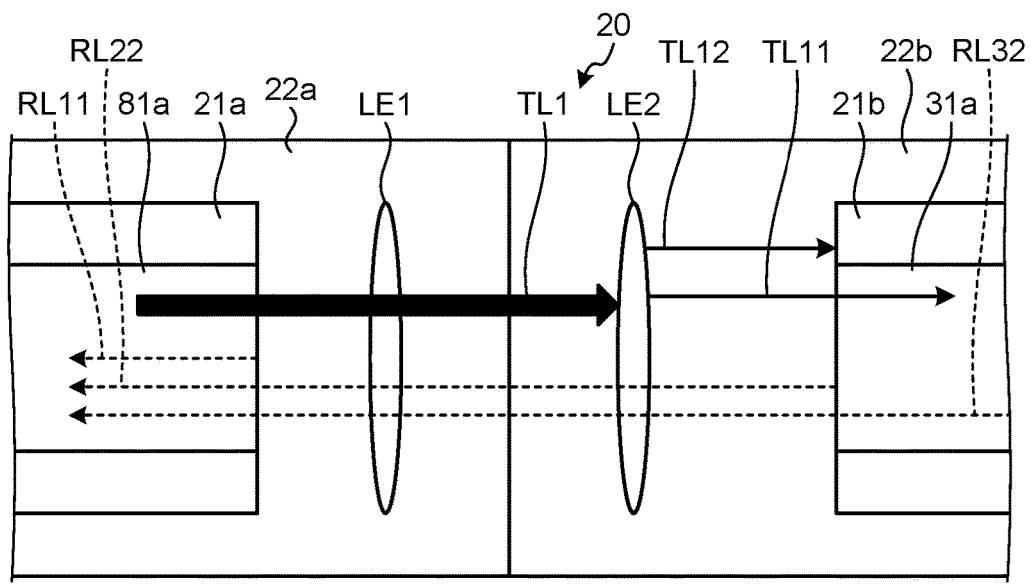
FIG. 4 is a schematic view illustrating an example of a state of connection of optical fibers in the connector.

FIG. 4 is a diagram schematically illustrating a configuration of the connector 20 and schematically illustrates a state in which, because the second optical fiber 31a does not fit normally, compared to the state illustrated in FIG. 3, the distance between the second lens LE2 and the second optical fiber 31a is long. Also in FIG. 4, the test light and reflected lights are represented by the arrows and illustration of the treatment light is omitted.

In the state illustrated in FIG. 4, when the test light TL1 is emitted from the first optical fiber 81a, part of the test light TL1 undergoes Fresnel reflection and serves as the reflected light RL11 and the reflected light RL11 propagates through the first optical fiber 81a. In the state illustrated in FIG. 4, the distance between the second lens LE2 and the second optical fiber 31a is longer than that in a normal state. For this reason, compared to the state in FIG. 3, a point of focus of the second lens LE2 is positioned on an upstream side with respect to a surface of incidence of the second optical fiber 31a in a direction in which the test light TL1 travels and part of the test light TL1 having passed through the second lens LE2 (a test light L12) is not incident on the second optical fiber 31a and light other than the test light TL12 (the test light TL11) is incident on the second optical fiber 31a. Part of the test light TL11 having reached the second optical fiber 31a undergoes Fresnel reflection at an incidence end of the second optical fiber 31a and serves as the reflected light RL22. The reflected light RL22 is incident on the inside of the first optical fiber 81a. When the reflected light RL22 is incident on the first optical fiber 81a, part of the reflected light RL22 undergoes Fresnel reflection.

The test light TL 11 having propagated through the second optical fiber 31a is reflected on the FBG 32 and serves as a reflected light RL32. The reflected light RL32 propagates through in a direction opposite to that of the test light TL11 in the second optical fiber 31a. The reflected light RL32 reaches the first optical fiber 81a via the second lens LE2 and the first lens LE1 and is incident on the inside of the first optical fiber 81a. When the reflected light RL32 is emitted from the second optical fiber 31a, part of the reflected light RL32 undergoes Fresnel reflection at an incidence end of the second optical fiber 31a. Also when the reflected light RL32 is incident on the first optical fiber 81a, part of the reflected light RL32 undergoes Fresnel reflection. The reflected light RL11, the reflected light RL22, and the reflected light RL32 are propagated to the photodiode 401 via the first optical fiber 81a, the optical multiplexer-demultiplexer 701, and the filter 601 and the intensity obtained by summing the intensities of the reflected light RL11, the reflected light RL22, and the reflected light RL32 having been propagated is measured by the measurement unit 1001.

When the intensity of the test light TL1 before being emitted from the first optical fiber 81a is 1, the transmittance of the pair of the first lens LE1 and the second lens LE2 is β, and the coupling efficiency based on the distance between the second lens LE2 and the second optical fiber 31a is x, in the case of the state illustrated in FIG. 4, the intensity obtained by summing the intensities of the reflected light RL11, the reflected light RL22, and the reflected light RL32 is obtained by Expression (2) that is presented below and that is obtained by adding the coupling efficiency x to Expression (1). The coupling efficiency x is 1 in the state in which the distance between the second lens LE2 and the second optical fiber 31a is normal, that is, the state in which the test light TL11 does not occur and is 0 in the state in which the distance between the second lens LE2 and the second optical fiber 31a is not normal and the test light TL1 is not incident on the second optical fiber 31a.

$$0.04+0.96*\beta*x*(0.04*\beta*x*0.96+ \\ 0.96*0.96*\beta*x*0.96) \qquad (2)$$

When β is 0.95 and the coupling efficiency is 0 to 1, the intensity that is obtained by summing the intensities of the reflected light RL11, the reflected light RL22, and the reflected light RL32 and that is measured by the measurement unit 1001 is an intensity within a range from 4% to 84% of that of the test light TL1. That is, when the intensity that is measured by the measurement unit 1001 is equal to or larger than 4% and smaller than 84%, it may be described that the first optical fiber 81a and the second optical fiber 31a are in a state of having a poor connection in the connector 20.

Figure 5:
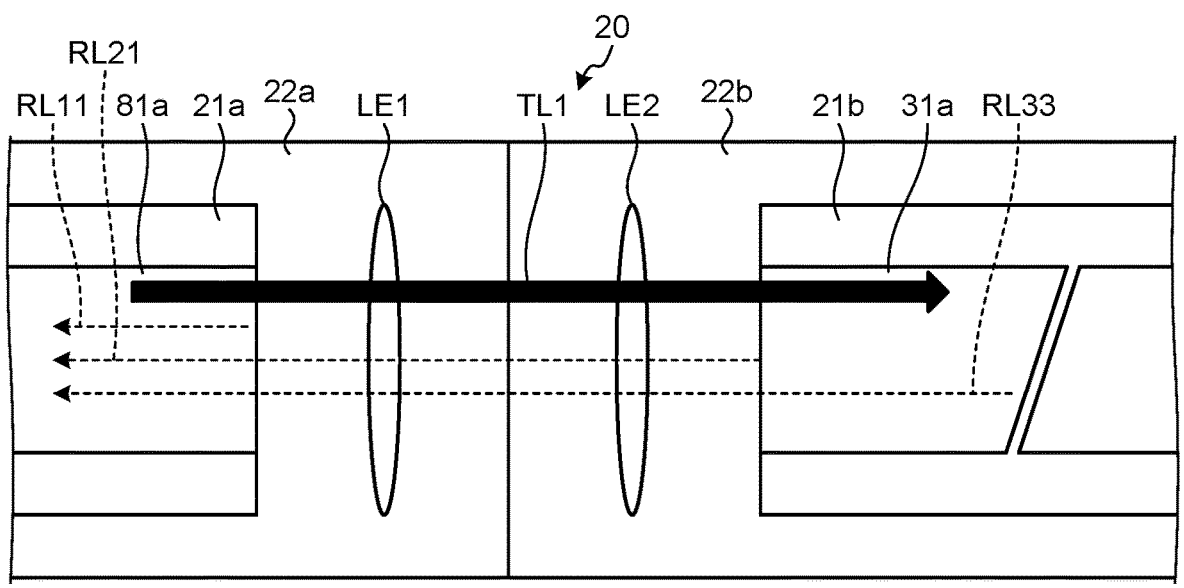
FIG. 5 is a schematic view illustrating an example of a state of connection of optical fibers in the connector.

FIG. 5 is a diagram schematically illustrating a configuration of the connector 20 and schematically illustrates a state in which the first optical fiber 81a and the second optical fiber 31a are connected normally and the second optical fiber 31a is broken. Also in FIG. 5, the test light and reflected lights are represented by the arrows and illustration of the treatment light is omitted.

When the second optical fiber 31a is broken, the test light TL1 having propagated through the second optical fiber 31a is reflected on a surface of the break in the second optical fiber 31a in some cases. The light reflected on the surface of the break is a reflected light RL33. The reflected light RL33 propagates through in a direction opposite to that of the test light TL1 in the second optical fiber 31a. The reflected light RL33 reaches the first optical fiber 81a via the second lens LE2 and the first lens LE1 and is incident on the inside of the first optical fiber 81a. When the reflected light RL33 is emitted from the second optical fiber 31a, part of the reflected light RL33 undergoes Fresnel reflection and, also when the reflected light RL33 is incident on the first optical fiber 81a, part of the reflected light RL33 undergoes Fresnel reflection. The reflected light RL11, the reflected light RL21, and the reflected light RL33 are propagated to the photodiode 401 via the first optical fiber 81a, the optical multiplexer-demultiplexer 701 and the filter 601 and the intensity obtained by summing the intensities of the reflected light RL11, the reflected light RL21, and the reflected light RL33 is measured by the measurement unit 1001.

When the intensity of the test light TL1 before being emitted from the first optical fiber 81a is 1, the transmittance of the pair of the first lens LE1 and the second lens LE2 is β, and the reflectivity on the surface of the break of the second optical fiber 31a is a, in the case of the state illustrated in FIG. 5, the intensity obtained by summing the intensities of the reflected light RL11, the reflected light RL21, and the reflected light RL33 is obtained by Expression (3) that is presented below and that is obtained by adding the reflectivity a to Expression (1).

$$0.04+0.96*\beta*(0.04*\beta*0.96+0.96*\alpha*0.96*\beta*0.96) \quad (3)$$

α is a value of 0 to 0.04 and therefore, when the first optical fiber 81a and the second optical fiber 31a are connected normally and the second optical fiber 31a is broken, the intensity that is obtained by summing the intensities of the reflected light RL11, the reflected light RL21, and the reflected light RL33 and that is measured by the measurement unit 1001 is an intensity within a range from 7.32% to 10.39% of that of the test light TL1. Note that, also in the case where the first optical fiber 81a and the second optical fiber 31a are not connected normally as in the state illustrated in FIG. 4, the measured intensity is within the range from 7.32% to 10.39% in some cases. Thus, when the intensity of the test light TL1 that is measured by the measurement unit 1001 is within the range from 7.32% to 10.39%, it may be described that the first optical fiber 81a and the second optical fiber 31a are in a state of having a poor connection in the connector 20 or in a state of being connected normally with the second optical fiber 31a being broken.

As described above, because the intensity of the reflected lights that is measured by the measurement unit 1001 differs according to the state of connection between the first optical fiber 81a and the second optical fiber 31a and the state of the second optical fiber 31a, it is possible to determine a state of connection between the first optical fiber 81a and the second optical fiber 31a and a state of the second optical fiber 31a. Particularly, while the intensity of the reflected lights that is measured by the measurement unit 1001 is 4% according to Expression (2) described above when the second optical fiber 31a is detached from the connector 20 completely, the intensity of the reflected lights that is measured by the measurement unit 1001 is 7.32 to 10.39% according to Expression (3) described above when the second optical fiber 31a is broken. As described above, because the intensity of the reflected lights that is measured by the measurement unit 1001 when the optical fiber is detached from the connector 20 is under the intensity of the reflected lights that is measured by the measurement unit 1001 when the optical fiber is disconnected, that is, when the optical fiber is broken, it is possible to distinguish the two states of detachment and disconnection completely.

Figure 6:
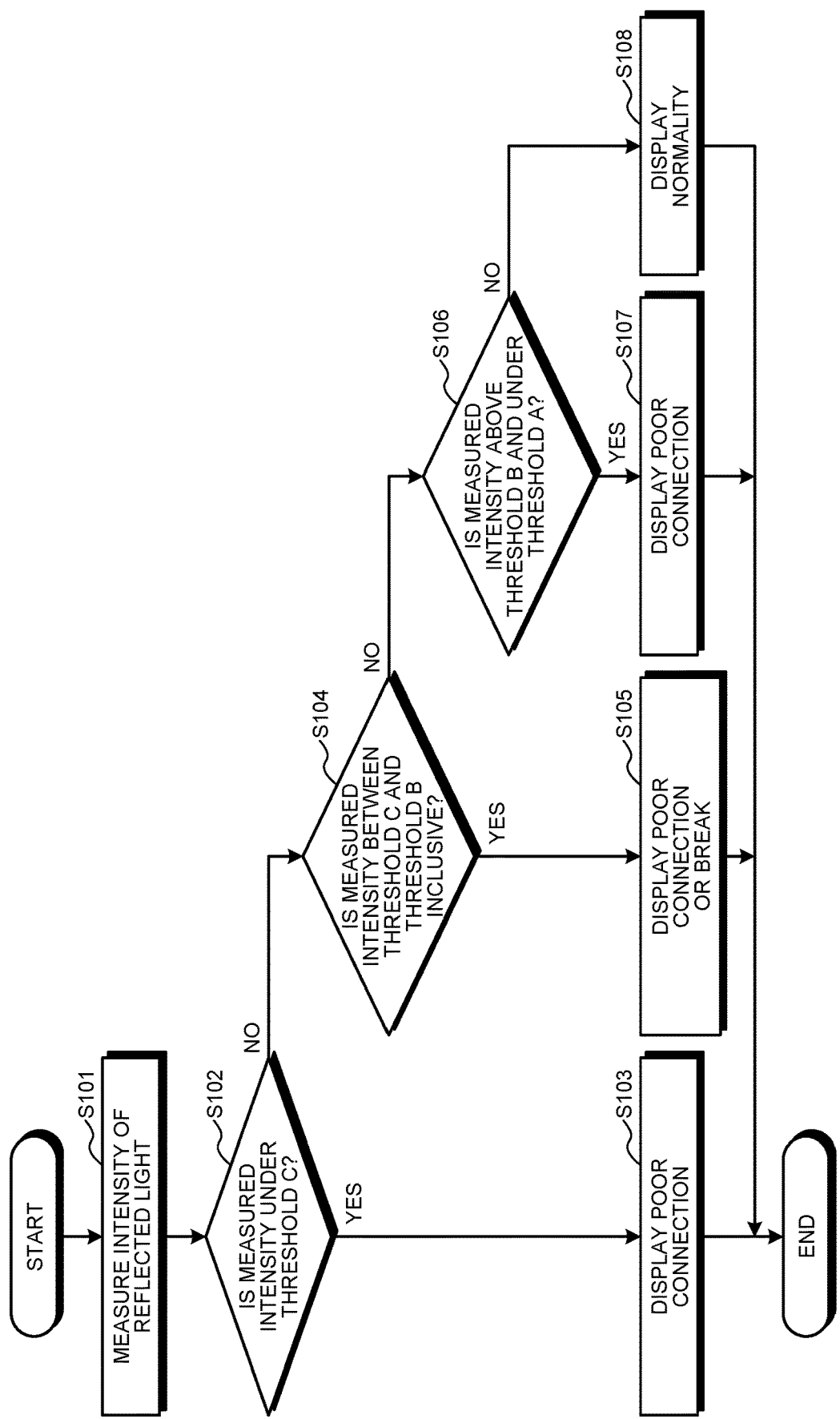
FIG. 6 is a flowchart illustrating a flow of a process of determining a state of connection.

FIG. 6 is a flowchart illustrating a flow of a process of determining a state of connection between the first optical fiber 81a and the second optical fiber 31a. The process illustrated in FIG. 6 is executed by the controller 100 and is performed when the controller 100 drives the first laser diode 301 and the second laser diode 302 and the treatment light and the test light are output.

First of all, at step S101, based on a current signal that is supplied from the photodiode 401, the controller 100 (the measurement unit 1001) measures an intensity of reflected light that is reflected and reaches the photodiode 401 in the test light TL1 that is output from the second laser diode 302.

The controller 100 (the determination unit 1002) then determines whether the measured intensity of the reflected lights is under a predetermined threshold C (step S102). The threshold C is stored in the storage unit. In the present embodiment, the threshold C is a value that is 7.32% of the intensity of the test light TL1. When the measured intensity is under the threshold C (YES at step S102), the controller 100 goes to step S103. Herein, the controller 100 determines that the first optical fiber 81a and the second optical fiber 31a have a poor connection.

At step S103, the controller 100 (the notification unit 1003) controls the display unit 200 and makes a notification that the first optical fiber 81a and the second optical fiber 31a are in the state of having a poor connection in the connector 20, using characters and symbols, and then ends the process in FIG. 6.

On the other hand, when the measured intensity is at or above the threshold C (NO at step S102), the controller 100 goes to step S104. The controller 100 determines whether the measured intensity of the reflected lights is between the threshold C and a predetermined threshold B inclusive at step S104. In the present embodiment, the threshold B is a value that is 10.39% of the intensity of the test light TL1. The threshold B is stored in the storage unit. When the measured intensity of the reflected lights is between the threshold C and a predetermined threshold B inclusive (YES at step S104), the controller 100 goes to step S105. The controller 100 determines here that the first optical fiber 81a and the second optical fiber 31a have a poor connection or the second optical fiber 31a is broken.

At step S105, the controller 100 controls the display unit 200 and makes a notification that the first optical fiber 81a and the second optical fiber 31a are in the state of having a poor connection in the connector 20 or the second optical fiber 31a is in a state of being broken, using characters and symbols, and then ends the process in FIG. 6. Note that, at step S105, the controller 100 may make a notification inducing checking the connection between the first optical fiber 81*a* and the second optical fiber 31*a*. The controller 100 may perform a process of stopping driving the first laser diode 301 before or after step S105.

When the measured intensity is an intensity above the threshold B (NO at step S104), the controller 100 goes to step S106. The controller 100 determines whether the measured intensity of the reflected lights exceeds the threshold B and under a predetermined threshold A at step S106. In the present embodiment, the threshold A is a value that is 84% of the intensity of the test light TL1. The threshold A is stored in the storage unit. The threshold A is an example of the first threshold.

When the measured intensity of the reflected lights exceeds the threshold B and is under the threshold A (YES at step S106), the controller 100 goes to step S107. The controller 100 determines here that the first optical fiber 81*a* and the second optical fiber 31*a* have a poor connection. At step S107, the controller 100 controls the display unit 200 and makes a notification that the first optical fiber 81*a* and the second optical fiber 31*a* are in the state of having a poor connection in the connector 20, using characters and symbols, and then ends the process in FIG. 6.

Note that, when the measured intensity is at or above the threshold A (NO at step S106), the controller 100 goes to step S108. The controller 100 determines here that the connection between the first optical fiber 81*a* and the second optical fiber 31*a* is normal and the second optical fiber 31*a* is not broken. At step S108, the controller 100 controls the display unit 200 and makes a notification that the connection between the first optical fiber 81*a* and the second optical fiber 31*a* in the connector 20 is in a normal state and that the second optical fiber 31*a* is not broken, using characters and symbols, and then ends the process in FIG. 6.

As described above, in the first embodiment, it is possible to determine, based on the result of measuring the intensity of the reflected lights having reflected and having reached the photodiode 401 in the test light TL1, a state of connection between the first optical fiber 81*a* and the second optical fiber 31*a* in the connector 20 and a state of the second optical fiber 31*a* in the connector 20 and notify the operator of the result of the determination.

Note that the values of the threshold A, the threshold B, and the threshold C are an example and are not limited to the above-described values. For example, when the second optical fiber 31*a* is broken and the distance between the second lens LE2 and the second optical fiber 31*a* is not normal, the measured intensity of the reflected lights is a value of 7.32% of the intensity of the test light TL1 in some cases. For this reason, when the measured intensity is at or under the threshold B, the controller 100 may determine that the first optical fiber 81*a* and the second optical fiber 31*a* have a poor connection or the second optical fiber 31*a* is broken and make a notification that the first optical fiber 81*a* and the second optical fiber 31*a* are in the state of having a poor connection in the connector 20 or the second optical fiber 31*a* is in the state of being broken, using characters and symbols. In the above-described embodiment, the value of the threshold A is a value that is 84% of the test light TL1, and, for example, the value may be a value that is 79% of the test light TL1 for an allowance for determination on connection. When the facet of the optical fiber has an AR (Anti-Reflection) coating, because the reflectivity to light on the facet of the optical fiber is lower than 4% that is the reflectivity in the case of Fresnel reflection, the values of the threshold A, the threshold B, and the threshold C may be set according to the coating. In the above-described embodiment, the wavelength of the treatment light is within the range of 600 nm to 1500 nm; however, when the facet of the optical fiber has an AR coating, the wavelength of the treatment light is preferably within a range of 900 nm to 1050 nm. When the wavelength of the treatment light is with the range of 900 nm to 1050 nm, reflection of the treatment light and the test light on the facet of the optical fiber may be inhibited with one type of AR coating.

In the present embodiment, every time the button of the operated unit 801 is operated by the operator, the second laser diode 302 may be driven to perform the process in FIG. 6. In the case of this configuration, for example, according to the process corresponding to the first operation on the button, the controller 100 determines that the first optical fiber 81*a* and the second optical fiber 31*a* are in the state of having poor connection or the second optical fiber 31*a* is in the state of being broken and, for example, on receiving the notification, the operator reconnects the optical fibers in the connector 20. Thereafter, the controller 100 performs the process in FIG. 6 according to the second operation on the button and, on determining that the first optical fiber 81*a* and the second optical fiber 31*a* are in the state of having a poor connection or the second optical fiber 31*a* is in the state of being broken, in other words, when determinations of a poor connection are successive with respect to the result of determination that is made for every operation, because it is considered that the poor connection is improved because the operator performs the reconnection, the controller 100 may determine that the second optical fiber 31*a* is broken and may make a notification that the second optical fiber 31*a* is in the state of being broken, using characters and symbols. According to this configuration, it is possible to notify the operator of the fact that the second optical fiber 31*a* is in the state of being broken.

In the first embodiment, as another example of poor connection of the optical fibers, the case where the test light TL12 that is not incident on the second optical fiber 31*a* occurs due to occurrence of axis misalignment of optical axis between the first lens LE1 and the second lens LE2 is assumed. For such a case, the coupling efficiency corresponding to the axis misalignment may be added as, for example, y to Expression (2) and the threshold A, the threshold B, and the threshold C may be set. The coupling efficiency y is, for example, 1 in the state where no axis misalignment occurs and is 0 in the state where the test light TL1 is not incident on the second optical fiber 31*a* due to axis misalignment.

Second Embodiment

A second embodiment of the present disclosure will be described next. In the second embodiment, compared to the first embodiment, the diameter of the first optical fiber 81*a* is smaller than the diameter of the second optical fiber 31*a* and the second embodiment is different in the method of connecting the first optical fiber 81*a* and the second optical fiber 31*a* in the connector 20 and in the process that is executed by the controller 100 and other configurations are the same as those of the first embodiment. Thus, in the following description, description of the same configuration as that of the first embodiment is omitted and the difference from the first embodiment will be described.

Figure 7:
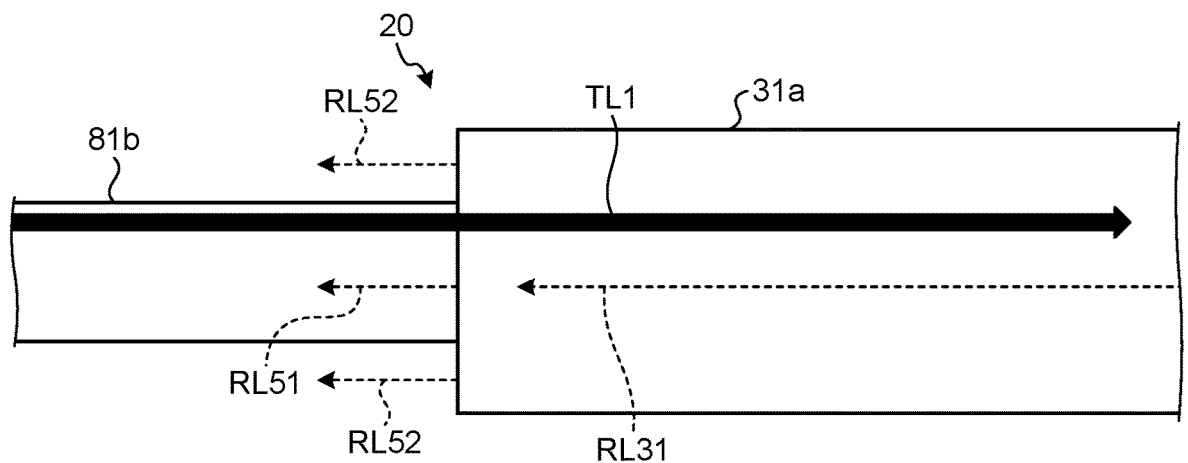
FIG. 7 is a schematic view illustrating an example of a state of connection of optical fibers in the connector.

FIG. 7 is a schematic view illustrating an example of a state of connection of optical fibers in the connector 20 according to the second embodiment. FIG. 7 illustrates a state of being connected normally without air gap between a first optical fiber 81*b* and the second optical fiber 31*a*. The first optical fiber 81*b* is an optical fiber with a core whose diameter is smaller than the diameter of the core of the second optical fiber 31a. The first optical fiber 81b is connected to the optical multiplexer-demultiplexer 701 and propagates a treatment light and a test light that are output from the optical multiplexer-demultiplexer 701. The first optical fiber 81b and the second optical fiber 31a are joined by a butt joint in the connector 20 with a sleeve and a ferrule of which illustration is omitted.

In FIG. 7, a test light and reflected lights are represented by the arrows and illustration of a treatment light is omitted. The test light TL1 is a test light that is output from the second laser diode 302. The test light TL1 is incident on the second optical fiber 31a from the first optical fiber 81b. The test light TL1 having propagated through the second optical fiber 31a is reflected on the FBG 32 and serves as the reflected light RL31. The reflected light RL31 propagates in a direction opposite to that of the test light TL1 in the second optical fiber 31a. The diameter of the core of the first optical fiber 81b is smaller than the diameter of the core of the second optical fiber 31a and therefore part of the reflected light RL31 is incident on the first optical fiber 81b. A reflected light RL51 illustrated in FIG. 7 represents a light that is incident on the core of the first optical fiber 81b in the reflected light RL31 and a reflected light RL52 illustrated in FIG. 7 represents a light that is not incident on the core of the first optical fiber 81b in the reflected light RL31. The reflected light RL51 is propagated to the photodiode 401 via the first optical fiber 81b, the optical multiplexer-demultiplexer 701, and the filter 601 and an intensity is measured by the measurement unit 1001.

When the intensity of the test light TL1 before being emitted from the first optical fiber 81b is 1, the reflectivity to the test light TL1 on the FBG 32 is 100%, and the connection loss due to the difference between the diameter of the core of the first optical fiber 81b and the diameter of the core of the second optical fiber 31a is γ, the intensity measured in the state illustrated in FIG. 7 is obtained by Expression (4) presented below.

$$1.00*\gamma \quad (4)$$

In the present embodiment, γ is the area ratio of the cross-sectional area of the core of the first optical fiber 81b and the cross-sectional area of the core of the second optical fiber 31a. For example, when the diameter of the core of the first optical fiber 81b is 105 μm and the diameter of the core of the second optical fiber 31a is 120 μm, γ is 0.766. When the state of connection of the first optical fiber 81b and the second optical fiber 31a is the state illustrated in FIG. 7 and γ=0.766, the intensity of the reflected light RL51 that is measured by the measurement unit 1001 is an intensity that is 76.6% of that of the test light TL1.

Figure 8:
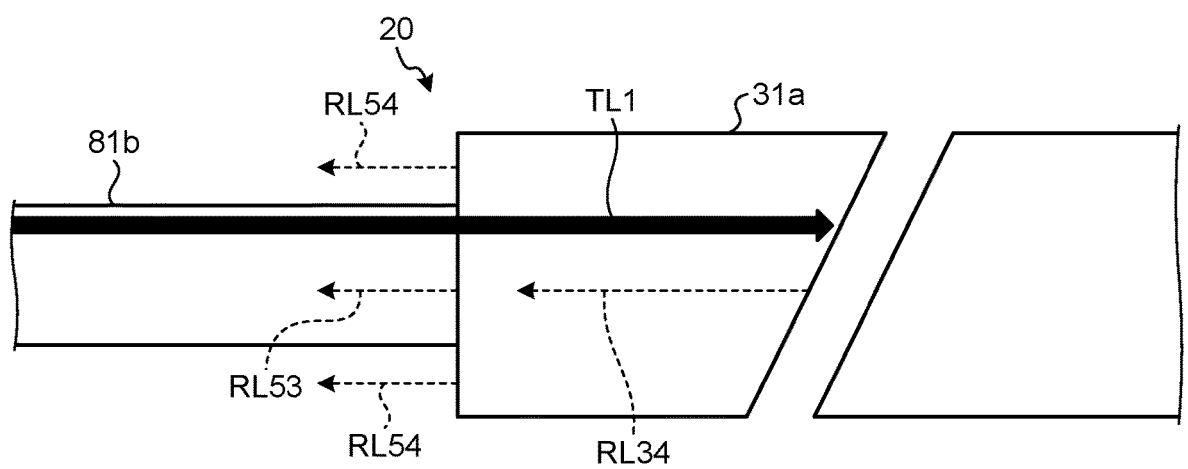
FIG. 8 is a schematic view illustrating an example of a state of connection of optical fibers in the connector.

FIG. 8 is a diagram schematically illustrating a state in which, while a connection is made normally without air gap between the first optical fiber 81b and the second optical fiber 31a in the connector 20, the second optical fiber 31a is broken. Also in FIG. 8, the test light and reflected lights are represented by the arrows and illustration of the treatment light is omitted.

As illustrated in FIG. 8, when the second optical fiber 31a is broken, the test light TL1 having propagated through the second optical fiber 31a is reflected on a surface of the break in the second optical fiber 31a in some cases. The light reflected on the surface of the break is a reflected light RL34. The reflected light RL34 propagates through in a direction opposite to that of the test light TL1 in the second optical fiber 31a. The diameter of the core of the first optical fiber 81b is smaller than the diameter of the core of the second optical fiber 31a and therefore part of the reflected light RL34 is incident on the first optical fiber 81b. A reflected light RL53 illustrated in FIG. 8 represents the light incident on the first optical fiber 81b in the reflected light RL34 and a reflected light RL54 illustrated in FIG. 8 represents the light not incident on the first optical fiber 81b in the reflected light RL34. The reflected light RL53 is propagated to the photodiode 401 via the first optical fiber 81b, the optical multiplexer-demultiplexer 701, and the filter 601 and an intensity is measured by the measurement unit 1001.

When the intensity of the test light TL1 before being emitted from the first optical fiber 81b is 1, the connection loss due to the difference between the diameter of the core of the first optical fiber 81b and the diameter of the core of the second optical fiber 31a is γ, and the reflectivity on the surface of the break of the second optical fiber 31a is α, the intensity measured in the state illustrated in FIG. 8 is obtained by Expression (5) presented below.

$$1.00*\gamma*\alpha \quad (5)$$

α is a value of 0 to 0.04 and therefore, when the state of connection of the first optical fiber 81b and the second optical fiber 31a is the state illustrated in FIG. 8 and γ=0.766, the intensity of the reflected light RL53 that is measured by the measurement unit 1001 is an intensity within a range of 0% to 3.06% of that of the test light TL1.

Figure 9:
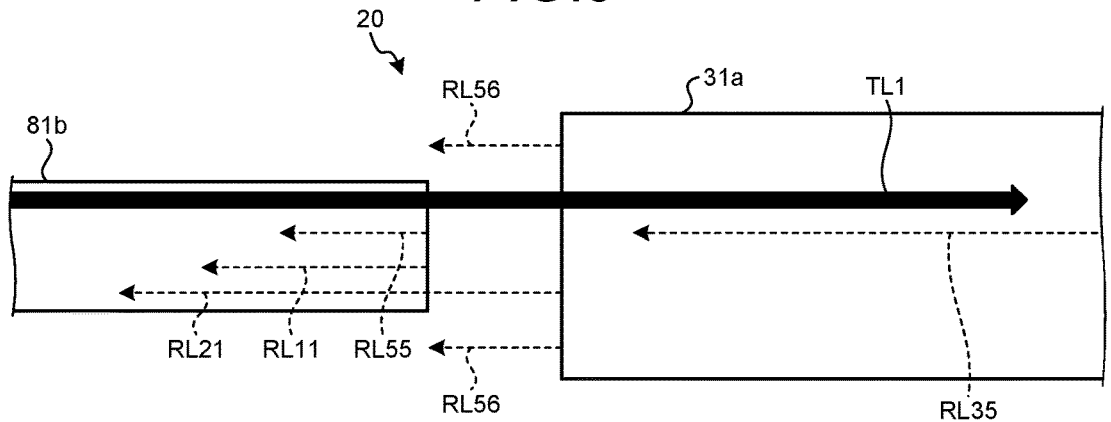
FIG. 9 is a schematic view illustrating an example of a state of connection of optical fibers in the connector.

FIG. 9 is a diagram schematically illustrating a state in which the second optical fiber 31a is not broken, there is an air gap between the first optical fiber 81b and the second optical fiber 31a, and thus a connection is not made normally. Also in FIG. 9, the test light and reflected lights are represented by the arrows and illustration of the treatment light is omitted.

In the state illustrated in FIG. 9, when the test light TL1 is emitted from the first optical fiber 81b, part of the test light TL1 undergoes Fresnel reflection and serves as the reflected light RL11 and the reflected light RL11 propagates through the first optical fiber 81b. Part of the test light TL1 that is emitted from the first optical fiber 81b undergoes Fresnel reflection at an end of incidence of the second optical fiber 31a and serves as the reflected light RL21. The reflected light RL21 is incident on the inside of the first optical fiber 81b. When the reflected light RL21 is incident on the first optical fiber 81b, part of the reflected light RL21 undergoes Fresnel reflection.

The light that is incident on the second optical fiber 31a in the test light TL1 propagates through the second optical fiber 31a, is reflected on the FBG32, and serves as a reflected light RL35. The reflected light RL35 propagates through in a direction opposite to that of the test light TL1 in the second optical fiber 31a. The reflected light RL35 is emitted from the second optical fiber 31a. When the reflected light RL35 is emitted from the second optical fiber 31a, part of the reflected light RL35 undergoes Fresnel reflection at an end of incidence of the second optical fiber 31a.

The diameter of the first optical fiber 81b is smaller than that of the second optical fiber 31a and therefore part of the reflected light RL35 that is emitted from the second optical fiber 31a is incident on the first optical fiber 81b. A reflected light RL55 illustrated in FIG. 9 represents the light incident on the first optical fiber 81b in the reflected light RL35 and a reflected light RL56 represents light not incident on the first optical fiber 81b in the reflected light RL35. Note that, also when the reflected light RL35 is incident on the first optical fiber 81b, part of the reflected light RL35 undergoes Fresnel reflection.

The reflected light RL11, the reflected light RL21, and the reflected light RL55 are propagated to the photodiode 401 via the first optical fiber 81*b*, the optical multiplexer-demultiplexer 701, and the filter 601 and the intensity that is obtained by summing the intensities of the reflected light RL11, the reflected light RL21, and the reflected light RL55 and that is measured by the measurement unit 100.

When the intensity of the test light TL1 before being emitted from the first optical fiber 81*b* is 1, the reflectivity of the test light TL1 on the FBG 32 is 100%, the connection loss due to the difference in diameter between the first optical fiber 81*b* and the second optical fiber 31*a* is $\gamma$, and the coupling efficiency between the first optical fiber 81*b* and the second optical fiber 31*a* is x, the intensity measured in the state illustrated in FIG. 9 is obtained by Expression (6) presented below. The coupling efficiency here is based on the air gap, the state in which the first optical fiber 81*b* and the second optical fiber 31*a* make contact with each other and all the test light TL1 is incident on the second optical fiber 31*a* is 1, and the state in which all the test light is not incident on the second optical fiber 31*a* is 0.

$$0.04 + x^2 * \gamma * 0.96^2 (0.04 + 0.96^2) \quad (6)$$

When $\gamma=0.766$, the intensity that is obtained by summing the intensities of the reflected light RL11, the reflected light RL21, and the reflected light RL55 and that is measured by the measurement unit 1001 is an intensity within a range from 4% to 71.2% of that of the test light TL1. In other words, when the intensity that is measured by the measurement unit 1001 is between 4% and 71.2% inclusive, it may be described that the first optical fiber 81*b* and the second optical fiber 31*a* are in the state of having a poor connection in the connector 20.

As described above, because the intensity of the reflected lights that is measured by the measurement unit 1001 differs according to the state of connection between the first optical fiber 81*b* and the second optical fiber 31*a* and the state of the second optical fiber 31*a*, it is possible to determine a state of connection between the first optical fiber 81*b* and the second optical fiber 31*a* and a state of the second optical fiber 31*a*. Particularly, while the intensity of the reflected lights that is measured by the measurement unit 1001 is 4% according to Expression (6) described above when the second optical fiber 31*a* is detached from the connector 20 completely, the intensity of the reflected lights that is measured by the measurement unit 1001 is 0 to 3.06% according to Expression (5) described above when the second optical fiber 31*a* is broken. As described above, because the intensity of the reflected lights that is measured by the measurement unit 1001 when the second optical fiber 31*a* is disconnected is under the intensity of the reflected lights that is measured by the measurement unit 1001 when the second optical fiber 31*a* is detached from the connector 20, it is possible to distinguish the two states of disconnection and detachment completely.

Figure 10:
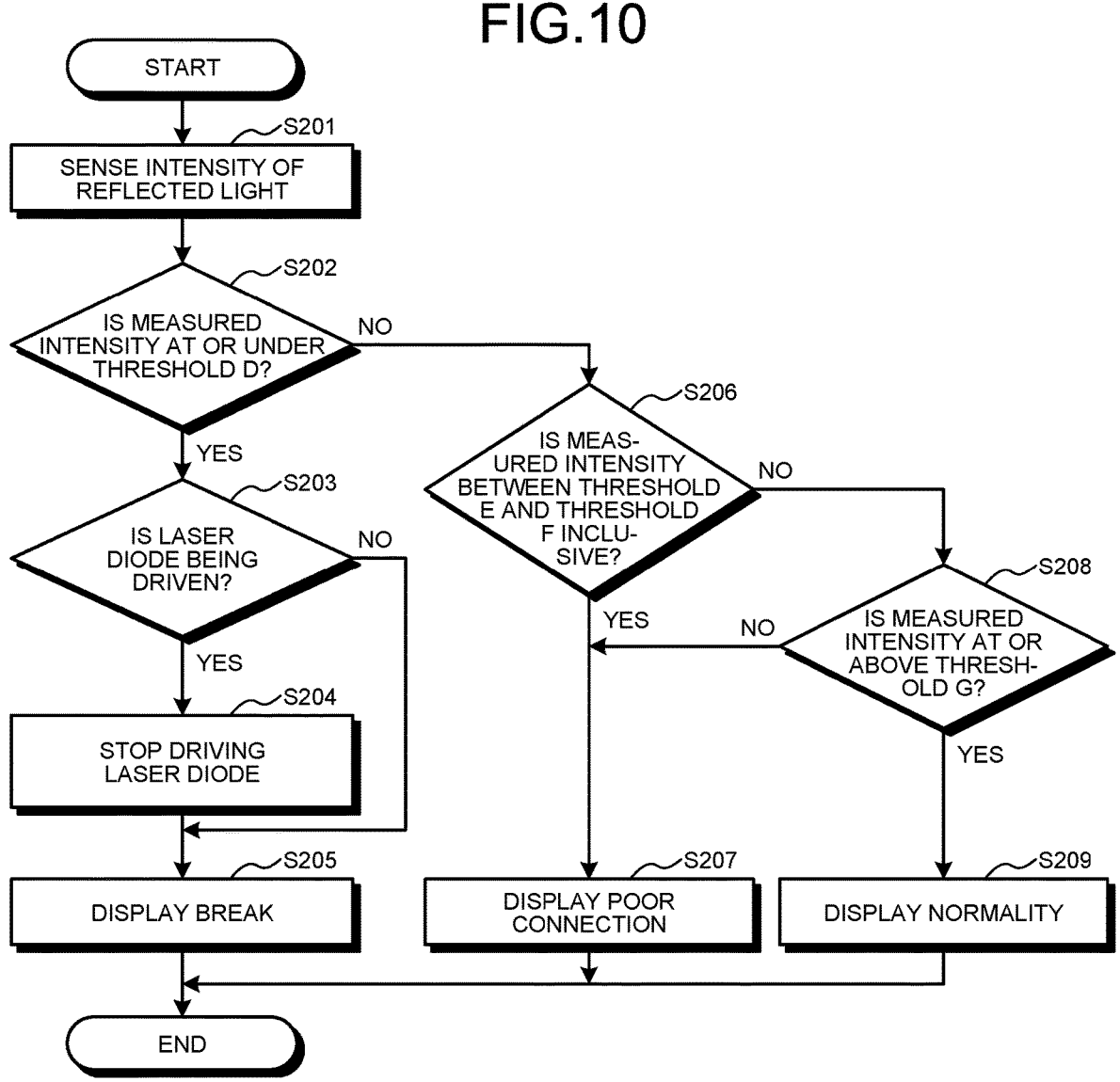
FIG. 10 is a flowchart illustrating a flow of a process of determining a state of connection.

FIG. 10 is a flowchart illustrating a flow of a process of determining a state of connection between the first optical fiber 81*b* and the second optical fiber 31*a*. The process illustrated in FIG. 10 is executed by the controller 100 and, for example, is performed when the controller 100 drives the first laser diode 301 and the second laser diode 302 and the treatment light and the test light are output.

First of all, at step S201, based on a current signal that is supplied from the photodiode 401, the controller 100 (the measurement unit 1001) measures an intensity of reflected light that is reflected and reaches the photodiode 401 in the test light TL1 that is output from the second laser diode 302.

The controller 100 (the determination unit 1002) then determines whether the measured intensity of the reflected light is at or under a predetermined threshold D (step S202). In the present embodiment, the threshold D is a value that is 3.06% of the intensity of the test light TL1. The threshold D is stored in the storage unit. The threshold D is stored in the storage unit. The threshold D is an example of a fourth threshold. When the measured intensity is at or under the threshold D (YES at step S202), the controller 100 goes to step S203. The controller 100 determines here that the second optical fiber 31*a* is broken.

At step S203, the controller 100 (the light source controller 1004) determines whether it is a state of driving at least one of the first laser diode 301 and the second laser diode 302. When it is the state of driving at least one of the first laser diode 301 and the second laser diode 302 (YES at step S203), the controller 100 goes to step S204 and, when it is a state of driving none of the first laser diode 301 and the second laser diode 302 (NO at step S203), the controller 100 goes to step S205.

When the controller 100 goes to step S204, the controller 100 stops driving the first laser diode 301 and the second laser diode 302 at step S204 and goes to step S205. At step S205, the controller 100 controls the display unit 200 and makes a notification of the state in which the optical fiber of the catheter 30 is broken, using characters and symbols, and then ends the process in FIG. 10.

On the other hand, when the measured intensity exceeds the threshold D (NO at step S202), the controller 100 goes to step S206. The controller 100 determines whether the measured intensity of the reflected light is between a predetermined threshold E and a predetermined threshold F inclusive at step S206. In the present embodiment, the threshold E is a value that is 4% of the intensity of the test light TL1 and the threshold F is a value that is 71.2% of the intensity of the test light TL1. The threshold E and the threshold F are stored in the storage unit. The threshold E is an example of a second threshold and the threshold F is an example of a third threshold. When the measured intensity of the reflected light is between the threshold E and the threshold F inclusive (YES at step S206), the controller 100 goes to step S207. The controller 100 determines here that the first optical fiber 81*b* and the second optical fiber 31*a* have a poor connection. At step S207, the controller 100 controls the display unit 200 and makes a notification that the optical fibers are in the state of having a poor connection in the connector 20, using characters and symbols, and then ends the process in FIG. 10.

When the measured intensity is not between the threshold E and the threshold F inclusive (NO at step S206), the controller 100 goes to step S208. The controller 100 determines whether the measured intensity of the reflected light is at or above a predetermined threshold G at step S208. In the present embodiment, the threshold G is a value that is 76.6% of the intensity of the test light L1. The threshold G is stored in the storage unit.

When the measured intensity of the reflected light is under the threshold G (NO at step S208), the controller 100 goes to step S207. The controller 100 determines here that the first optical fiber 81*b* and the second optical fiber 31*a* have a poor connection. When the measured intensity of the reflected light is at or above the threshold G (YES at step S208), the controller 100 goes to step S209. The controller 100 determines here that the connection between the first optical fiber 81*b* and the second optical fiber 31*a* is normal and the second optical fiber 31*a* is not broken. At step S209, the controller 100 controls the display unit 200 and makes a notification that the connection between the optical fibers in the connector 20 is in a normal state and that the optical fiber is not broken, using characters and symbols, and then ends the process in FIG. 10.

In the case where, while it is the state without airgap between the first optical fiber 81*b* and the second optical fiber 31*a*, the first optical fiber 81*b* and the second optical fiber 31*a* have axis misalignment, the intensity that is measured by the measurement unit 1001 corresponds to Expression (7) that is presented below and that is obtained by adding a coupling efficiency x based on the axis misalignment to Expression (4) described above.

$$1.00 * \gamma * x^2 \tag{7}$$

x is within a range of 0 to 1 and x=1 when there is no loss when the test light TL1 is incident on the second optical fiber 31*a* from the first optical fiber 81*b* and the intensity of the reflected light that is measured by the measurement unit 1001 is an intensity that is 76.6% of that of the test light TL1. In the case where there is a loss when the first optical fiber 81*b* and the second optical fiber 31*a* are misaligned and the test light TL1 is incident on the second optical fiber 31*a* from the first optical fiber 81*b* and when the reflected light that is reflected on the FBG 32 is incident on the first optical fiber 81*b* from the second optical fiber 31*a*, the value of x is smaller than 1 and the intensity of the reflected light that is incident on the first optical fiber 81*b* is an intensity that is smaller than 76.6% of that of the test light TL1. For this reason, when the measured intensity of the reflected light is at or above the threshold E and is under the threshold G, for example, at step S206, the controller 100 may go to step S207. In this case, the controller 100 determines that the first optical fiber 81*b* and the second optical fiber 31*a* are in the state of having poor connection.

In the second embodiment, it is possible to, based on the result of measuring the intensity of the reflected light that is reflected and that is incident on the first optical fiber 81*b* in the test light TL1, determine a state of connection between the first optical fiber 81*b* and the second optical fiber 31*a* in the connector 20 and the state of the second optical fiber 31*a* and notify the operator of the result of the determination.
Modification.

The embodiments of the present disclosure have been described above and the present disclosure is not limited to the embodiments described above and the present disclosure may be carried out in other various modes. For example, the above-described embodiments may be modified as follows to carry out the present disclosure. Note that each of the above-described embodiments and the following modifications may be combined. What configured by combining components of each of the above-described embodiments and each of the modifications is covered by the present disclosure. Further effects and modifications may be derived easily by those skilled in the art. Wider modes of the present disclosure are not limited to the above-described embodiments and the modifications and various changes may be made.

In the first embodiment described above, the threshold A is a value that is 84% of the intensity of the test light TL1 and, for an allowance for determination on connection, the value of the threshold A may be, for example, a value that is 79% of the intensity of the test light TL1.

In the second embodiment described above, the diameter of the core of the first optical fiber 81*b* and the diameter of the core of the second optical fiber 31*a* are different from each other; however, the diameter of the core of the first optical fiber 81*b* and the diameter of the core of the second optical fiber 31*a* may be set equal and a butt joint may be made. In this case, the value of y is 1 in Expressions (4) to (6) described above. In this case, the values of the threshold D, the threshold E, the threshold F, and the threshold G may be set according to the values that may be taken when $\gamma=1$ in Expressions (4) to (6).

In the second embodiment, the first optical fiber 81*b* and the second optical fiber 31*a* are connected by a butt joint; however, instead of the butt joint, a configuration of space coupling using lenses as in the first embodiment may be employed. In this case, according to the transmittance of the pair of the first lens LE1 and the second lens LE2, the coupling efficiency depending on an air gap and axis misalignment, Fresnel reflection, and the area ratio between the first optical fiber 81*b* and the second optical fiber 31*a*, thresholds of a determination on a break in the optical fiber, a determination on poor connection of the optical fibers, and a determination on normal connection of the optical fibers may be determined and each of the determinations may be made according to the determined thresholds.

In the above-described first embodiment, in the case where the measured intensity is under the threshold A, the controller 100 may determine that the first optical fiber 81*a* and the second optical fiber 31*a* have a poor connection even if the intensity is any value. In this case, for example, when notifications of poor connection are successive even if an operator reconnects the first optical fiber 81*a* and the second optical fiber 31*a* in the connector 20, the operator is able to determine that there is no poor connection but the second optical fiber 31*a* is broken.

In the above-described embodiment, the display unit 200 makes a notification of a poor connection of the optical fibers and a notification that the optical fiber is broken; however, the laser device 10 may be provided with a speaker and the speaker may make a notification of a poor connection of the optical fibers and a notification that the optical fiber is broken with the speaker by sound with the speaker.

In the first embodiment and the second embodiment described above, the number of the first laser diodes 301 serving as the light source of the treatment light is one; however, the number of the first laser diodes 301 may be more than one. When the number of the first laser diodes 301 may be more than one, treatment lights that are output from a plurality of the first laser diodes 301 may be multiplexed by the multiplexer and may be input to the optical multiplexer-demultiplexer 701.

In the above-described embodiment, before being input to the optical multiplexer-demultiplexer 701, the treatment light is multiplexed with the test light; however, the treatment light may be multiplexed with the test light between the optical multiplexer-demultiplexer 701 and the connector 20. The optical multiplexer-demultiplexer 701 may be configured to multiplex a plurality of lights spatially or may perform multiplexing by an optical combiner, or the like.

The filter 601 is unnecessary in some cases depending on the configuration. For example, when the optical multiplexer-demultiplexer 701 is a WDM coupler, because the extinction ratio is high and efficient demultiplexing is enabled, a configuration in which the filter 601 is not provided may be employed.

The above-described embodiment is not limited to a system that outputs laser light for treatment and is applicable to a system that connects an optical fiber detachably with a connector and outputs laser light.

Figure 11:
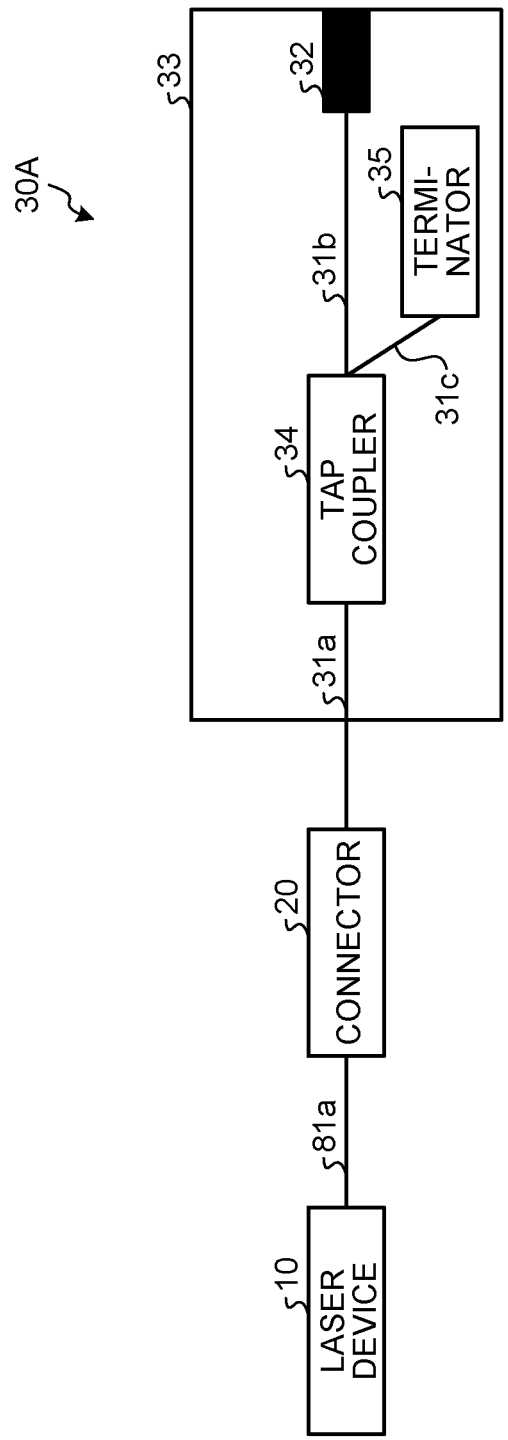
FIG. 11 is a diagram illustrating a configuration of a catheter according to a modification.

In the above-described embodiment, the catheter may be configured to include a tap coupler. FIG. 11 is a diagram illustrating a configuration of a catheter 30A that includes a tap coupler 34. Note that, in FIG. 11, the same elements as those of the catheter 30 are denoted with the same reference numerals. The catheter 30A includes the second optical fiber 31a, an optical fiber 31b, an optical fiber 31c, the FBG 32, the catheter body 33, the tap coupler 34, and a terminator 35. The optical fiber 31b is an example of a second optical fiber. The terminator 35 is an example of a reflector.

The tap coupler 34 is an asymmetric tap coupler with 1×2 ports and a branching ratio of 90:10. In the tap coupler 34, the optical fiber 31b is connected to a main port with a large ratio of the branched light. The test light TL1 having propagated through the optical fiber 31b is reflected on the FBG 32 and propagates through in a direction opposite to that of the test light TL1 and propagates to the laser device 10 via the tap coupler 34, the second optical fiber 31a, the connector 20, and the first optical fiber 81a.

In the tap coupler 34, the optical fiber 31c is connected to a sub port with a small ratio of the branched light. The terminator 35 that performs a termination process of the optical fiber is connected to a distal end of the optical fiber 31c.

A reflective film may be formed on the terminator 35 such that the reflectivity of the test light TL1 having propagated via the tap coupler 34 is 95% or larger. In this configuration, when the optical fiber 31b is broken, the reflected light that is reflected on the surface of the break and the reflected light from the terminator 35 propagate to the laser device 10. Even when the optical fiber 31b is disconnected, because there is the reflected light from the terminator 35, the intensity of the reflected light that is measured by the measurement unit 1001 when the second optical fiber 31a is detached from the connector 20 is under the intensity of the reflected light that is measured by the measurement unit 1001 when the optical fiber 31b is disconnected. Thus, as in the first embodiment, it is possible to distinguish the two states of detachment and disconnection completely.

Note that the terminator 35 may be a distal end part of the optical fiber 31c that is cut obliquely such that the reflectivity to the test light TL1 is 4% or smaller. In this configuration, when the optical fiber 31b is broken, the reflected light that is reflected on the surface of the break propagates to the laser device 10. The test light TL1 having propagated through the optical fiber 31b is branched by the tap coupler 34 and the intensity lowers and therefore the reflected light that is reflected on the surface of the break of the optical fiber 31b and that propagates to the laser device 10 lowers, too. On the other hand, because the reflectivity of the terminator 35 is low, the test light TL1 having reached the terminator 35 does not propagate to the laser device 10 even when the test light TL1 is reflected on the terminator 35. In the case where the reflected light of the test light TL1 does not propagate to the laser device 10 from the terminator 35 as described above, the intensity of the reflected light that is measured by the measurement unit 1001 when the optical fiber 31b is disconnected is under the intensity of the reflected light that is measured by the measurement unit 1001 when the second optical fiber 31a is detached from the connector 20. Thus, as in the second embodiment, it is possible to distinguish the two states of detachment and disconnection completely.

The present disclosure may be used for an optical fiber connection state determination system and an optical fiber connection state determination method.

According to the present disclosure, an effect that it is possible to determine a state of connection of a detachable optical fiber.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An optical fiber connection state determination system for determining a state of connection between a first optical fiber configured to propagate a test light input from a light source and a second optical fiber in a connector configured to detachably connect an output side from which the test light is output in the first optical fiber and an input side of the second optical fiber to which the test light propagated by the first optical fiber and output from the first optical fiber is input, comprising:
   measurement circuitry configured to measure an intensity of a reflected light reflected and propagating through the first optical fiber in the test light; and
   determination circuitry configured to determine the state of connection between the first optical fiber and the second optical fiber in the connector based on the intensity measured by the measurement circuitry,
   wherein the determination circuitry is configured to determine the state of connection every time the measurement circuitry performs a measurement and, when results of determination of poor connection are successive, the determination circuitry is configured to determine that the second optical fiber is broken.

2. The optical fiber connection state determination system according to claim 1, wherein the intensity of the reflected light measured by the measurement circuitry differs between a case where the second optical fiber is disconnected and a case where the second optical fiber is detached from the connector.

3. The optical fiber connection state determination system according to claim 2, wherein the intensity of the reflected light measured by the measurement circuitry in the case where the second optical fiber is disconnected is larger than the intensity of the reflected light measured by the measurement circuitry in the case where the second optical fiber is detached from the connector.

4. The optical fiber connection state determination system according to claim 1, wherein the first optical fiber and the second optical fiber are coupled spatially in the connector, and
   when the intensity is under a first threshold, the determination circuitry is configured to determine that the first optical fiber and the second optical fiber have a poor connection.

5. The optical fiber connection state determination system according to claim 3, wherein
   an optical fiber coupler is connected to the second optical fiber, and
   the test light emitted from a predetermined port among a plurality of ports from which the test light is emitted in the fiber coupler is reflected on a reflector configured to reflect the test light.

6. The optical fiber connection state determination system according to claim 3, wherein
   the measurement circuitry is configured to perform a measurement every time an operator performs an operation of measurement.

7. The optical fiber connection state determination system according to claim 2, wherein the intensity of the reflected light measured by the measurement circuitry in the case where the second optical fiber is detached from the connector is larger than the intensity of the reflected light measured by the measurement circuitry in the case where the second optical fiber is disconnected.

8. The optical fiber connection state determination system according to claim 7, wherein
the first optical fiber and the second optical fiber are joined by a butt joint in the connector, and
when the intensity is equal to or greater than a second threshold and less than or equal to a third threshold that is larger than the second threshold, the determination circuitry is configured to determine that the first optical fiber and the second optical fiber have a poor connection.

9. The optical fiber connection state determination system according to claim 7, wherein an optical fiber coupler is connected to the second optical fiber.

10. The optical fiber connection state determination system according to claim 8, wherein, when the intensity is at or under a fourth threshold smaller than the second threshold, the determination circuitry is configured to determine that the second optical fiber is broken.

11. The optical fiber connection state determination system according to claim 1, further comprising notification circuitry configured to notify the state of connection between the first optical fiber and the second optical fiber according to a result of determination by the determination circuitry.

12. The optical fiber connection state determination system according to claim 1, wherein
a laser light that cauterizes a human body is multiplexed with the test light and is input to the first optical fiber, and
when the determination circuitry determines that the second optical fiber is broken, the determination circuitry is configured to stop output of the laser light from a light source configured to output the laser light.

13. An optical fiber connection state determination method for determining a state of connection between a first optical fiber that propagates a test light input from a light source and a second optical fiber in a connector configured to detachably connect an output side from which the test light is output in the first optical fiber and an input side of the second optical fiber to which the test light propagated by the first optical fiber and output from the first optical fiber is input, the method comprising:
measuring an intensity of a reflected light reflected and that propagates through the first optical fiber in the test light; and
determining the state of connection between the first optical fiber and the second optical fiber based on the intensity measured at every measurement, wherein,
when results of determination of poor connection are successive, the determining includes determining that the second optical fiber is broken.

* * * * *